United States Patent [19]

Levitt

[11] 4,443,244

[45] Apr. 17, 1984

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 370,395

[22] Filed: Apr. 21, 1982

Related U.S. Application Data

[62] Division of Ser. No. 151,245, Jul. 13, 1982, Pat. No. 4,339,266, which is a division of Ser. No. 840,167, Oct. 6, 1977, Pat. No. 4,257,802.

[51] Int. Cl.³ .................... A01N 43/66; C07D 409/12
[52] U.S. Cl. .......................................... 71/93; 544/212
[58] Field of Search ............................ 544/212; 71/93

[56] References Cited

U.S. PATENT DOCUMENTS

| | | | |
|---|---|---|---|
| 4,127,405 | 11/1978 | Levitt | 544/211 |
| 4,190,432 | 2/1980 | Levitt | 71/93 |
| 4,214,890 | 7/1980 | Levitt | 71/93 |
| 4,231,784 | 11/1980 | Levitt | 71/93 |

*Primary Examiner*—John M. Ford

[57] ABSTRACT

N-(heterocyclicaminocarbonyl)arylsulfonamides in which at least one of the acyclic nitrogens thereof is substituted by lower alkyl, or sometimes in the case of aminocarbonyl nitrogen, by methoxy; e.g. N-[N-(4,6-dimethoxy-1,3,5-triazin-2-yl)-N-methylaminocarbonyl]-2-chlorobenzenesulfonamide or N-[N-(4,6-dimethoxy-1,3,5-triazin-2-yl)-N-methylaminocarbonyl]-2-nitrobenzenesulfonamide; are useful for the regulation of plant growth and as general and selective herbicides.

12 Claims, No Drawings

HERBICIDAL SULFONAMIDES

This application is a divisional of my copending application U.S. Ser. No. 151,245, filed July 13, 1982 (now U.S. Pat. No. 4,339,266) which in turn is a divisional of application Ser. No. 840,167, filed Oct. 6, 1977 (now U.S. Pat. No. 4,257,802).

BACKGROUND

This invention relates to novel N-(heterocyclicaminocarbonyl)arysulfonamides in which at least one of the acyclic nitrogens thereof is substituted by lower alkyl, or in some cases by methoxy. The compounds of this invention and their agriculturally suitable salts, are useful as agricultural chemicals, such as plant growth regulants and herbicides.

Netherlands Pat. No. 121,788, published Sept. 15, 1966, discloses the preparation of compounds of the following Formula and their use as general or selective herbicides,

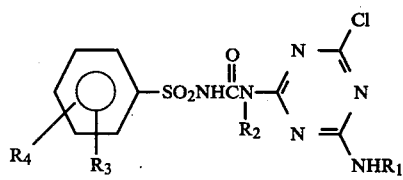

wherein $R_1$ and $R_2$ may independently be alkyl of 1–4 carbon atoms; and $R_3$ and $R_4$ may independently be hydrogen, chlorine or alkyl of 1–4 carbon atoms.

U.S. Pat. No. 3,637,366 discloses compounds having the formula:

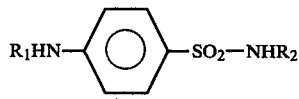

wherein $R_1$ is hydrogen or lower saturated aliphatic acyl and $R_2$ is hydrogen, 2-pyrimidinyl, pyridyl, amidino, acetyl or carbamoyl. The disclosed compounds are said to provide control of crabgrass, cress, endive, clover and *Poa annua*.

French Pat. No. 1,468,747 discloses the following para-substituted phenylsulfonamides as being useful as antidiabetic agents:

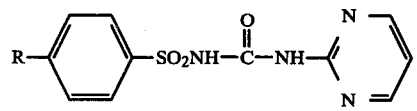

wherein R=H, halogen, $CF_3$ or alkyl.

Compounds of the following formula, and their use as antidiabetic agents, are reported in J. Drug Res. 6, 123 (1974).

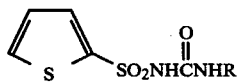

wherein R is pyridyl.

Logemann et al. Chem Ab., 53, 18052 g (1959), disclose a number of sulfonamides, including uracil derivatives and those having the formula:

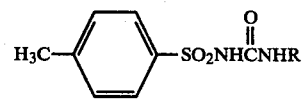

wherein R is butyl, phenyl or

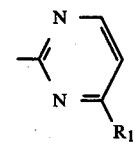

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121–5 (1962) [Chem. Ab., 59 1633 e] describes the synthesis of N-[(2,6-dimethoxypyrimidin-4-yl)aminocarbonyl]-4-methyl-benzenesulfonamide:

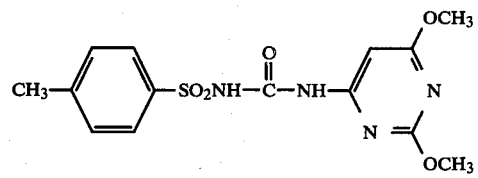

Based upon similarity to a known compound, the author predicted hypoglycemic activity for the foregoing compound.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

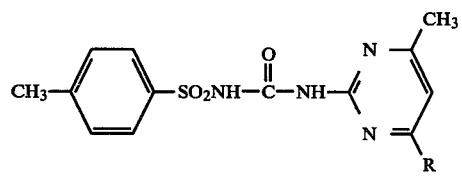

wherein R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency.

A wide variety of materials useful for killing or inhibiting (controlling) the growth of undesired vegetation is available; such materials are commonly referred to as herbicides. However, the need still exists for effective herbicides that destroy or control weeds while not significantly damaging useful crops. Some weeds (nutsedge is a particular example) are very difficult to control; many of the herbicides that are used to control nutsedge are so nonselective that they cause damage to the crops themselves.

SUMMARY OF THE INVENTION

According to this invention, there are provided novel compounds of Formula I and their agriculturally suitable salts, suitable agricultural compositions containing them and methods of using them as general and selective herbicides having both preemergence and postemergence activity, as well as plant growth regulants.

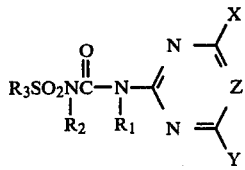

wherein $R_1$ is H, alkyl of one to three carbon atoms or —$OCH_3$;

$R_2$ is H or alkyl of one to three carbon atoms;

$R_3$ is

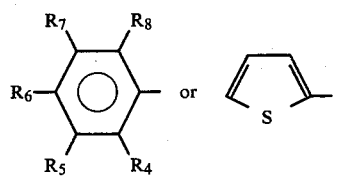

$R_4$ and $R_7$ are independently hydrogen, fluorine, chlorine, bromine, alkyl of 1–4 carbon atoms, alkoxy of 1–4 carbon atoms, nitro, $CF_3$, $CH_3S$— or $CH_3CH_2S$—;

$R_5$, $R_6$ and $R_8$ are independently hydrogen, fluorine, chlorine, bromine or methyl;

X is Cl, $CH_3$, —$CH_2CH_3$, alkoxy of one to three carbons, $CF_3$, $CH_3S$—, $CH_3OCH_2$— or $CH_3OCH_2CH_2O$—;

Y is $CH_3$ or $OCH_3$;

Z is CH or N;

and their agriculturally suitable salts; provided that:

(a) $R_1$ and $R_2$ may not simultaneously be hydrogen; and (b) when $R_4$ and $R_8$ are both hydrogen, at least one of $R_5$, $R_6$ or $R_7$ must be hydrogen;

(c) when $R_6$ os other than H, at least one or $R_4$, $R_5$, $R_7$ and $R_8$ is other than H and at least two of $R_4$, $R_5$, $R_7$ and $R_8$ must be hydrogen; and (d) when $R_6$ is H and all of $R_4$, $R_5$, $R_7$ and $R_8$ are other than H, then all of $R_4$, $R_5$, $R_7$ and $R_8$ must be either Cl or $CH_3$.

Preferred in order of increasing preference based on activity or cost, or both, are:

(1) those compounds of Formula I defined above wherein $R_1$ and $R_2$ are independently H or $CH_3$;

X is $CH_3$, $CH_3CH_2$— or alkoxy of one to three carbons; and

Y is $CH_3$ or $OCH_3$;

(2) compounds of preference (1) wherein

X and Y are independently $CH_3$ or $OCH_3$;

$R_1$ is $CH_3$; and $R_2$ is H;

(3) compounds of preference (2) wherein

X is $OCH_3$; and

Y is $CH_3$ or $OCH_3$;

(4) compounds of Formula I wherein $R_3$ is

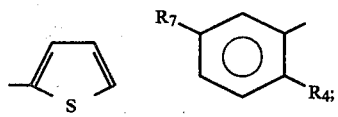

(5) compounds of preferance (4) wherein $R_3$ is

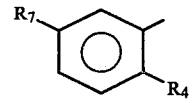

(6) compounds of preference (5) wherein $R_4$ is Cl, $CH_3$ or $NO_2$; and $R_7$ is H, Cl or $CH_3$;

(7) compounds of Formula I defined above wherein $R_1$ is $CH_3$;

$R_2$ is H;

$R_3$ is 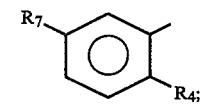

$R_4$ is Cl, $CH_3$ or $NO_2$;

$R_7$ is H, Cl or $CH_3$;

X is $OCH_3$; and

Y is $CH_3$ or $OCH_3$.

Specifically preferred for their outstanding herbicidal activity, or very favorable cost, or both, are:

(1) N-[N-(4,6-dimethoxy-1,3,5-triazin-2-yl)-N-methylaminocarbonyl]-2-chlorobenzenesulfonamide.

(2) N-[N-(4,6-dimethoxy-1,3,5-triazin-2-yl)-N-methylaminocarbonyl]-2-nitrobenzenesulfonamide.

(3) N-[N-(4-(4-methoxy-6-methylpyrimidin-2-yl)-N-methylaminocarbonyl]-2-chlorobenzenesulfonamide.

(4) N-[N-(4-methoxy-6-methylpyrimidin-2-yl)-N-methylaminocarbonyl]-2-nitrobenzenesulfonamide.

Synthesis

As shown in Equation 1, the compounds of Formula I, wherein $R_2$ is H, can be prepared by reacting an appropriately substituted sulfonyl isocyanate of Formula II with an appropriate 2-alkylaminopyrimidine or 2-alkylamino-1,3,5-triazine of Formula III, $R_1$, $R_3$, X, Y and Z being as previously defined.

Equation 1

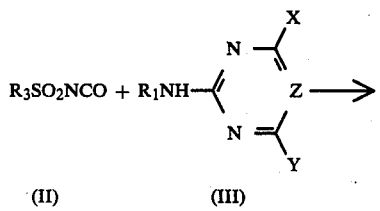

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine III. Since each isocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

Compounds of Formula I, wherein $R_2$ is alkyl, can be prepared by alkylation of the salts of compounds of Formula I, wherein $R_2$ is H, as shown in Equation 2; $R_1$, $R_2$, $R_3$, X, Y and Z being as previously defined and M is a metal cation and Q an anion, such as halide or sulfate.

Equation 2

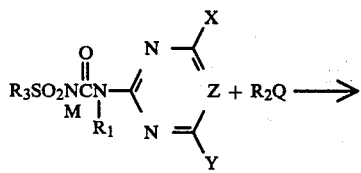

The reaction is best carried out in aprotic organic solvents such as tetrahydrofuran, dimethylformamide, or dimethylacetamide, at ambient pressure and temperature. Alkylating agents such as dimethyl sulfate, methyl iodide, and ethyl iodide can be employed. The desired product can be isolated by pouring the reaction mixture into water and filtering off the precipitated solid.

Alternatively, compounds of Formula I, wherein $R_2$ is alkyl, can be prepared by the reaction of an appropriately substituted sulfonyl-N-alkylcarbamyl chloride of Formula IV with an appropriate 2-aminopyrimidine or 2-amino-1,3,5-triazine of Formula III; as shown in Equation 3; $R_1$, $R_2$, $R_3$, A, X and Z are as previously defined.

Equation 3

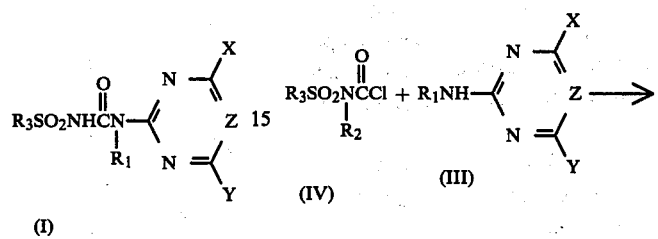

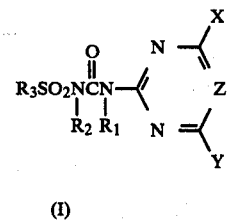

The preparation of ureas from amines and carbamyl chlorides is well known to the art. The reaction can best be carried out by adding equivalent amounts of a carbamyl chloride, IV, and amine, III, to an inert organic solvent, such as tetrahydrofuran, xylene, or methylene chloride, in the presence of acid acceptor, such as triethylamine, pyridine, or sodium carbonate employing temperatures from 20°-130°. Soluble products can be isolated by filtering off precipitated salts and concentration of the filtrate. Insoluble products can be filtered off and washed free of salts with water.

The intermediate sulfonyl-N-alkyl carbamyl chlorides of Formula IV can be prepared by phosgenation of N-alkylsulfonamide salts. The sulfonamide salt is added to an excess of phosgene in an inert organic solvent, such as tetrahydrofuran, toluene, or xylene, whereupon the carbamyl chloride can be isolated or reacted in situ with the amine, III, after removal of the excess phosgene.

The preparation of agriculturally suitable salts of the compounds of Formula I, as well as starting materials and intermediates for said compounds is disclosed in my applications Ser. No. 824,805 filed Aug. 15, 1977 and Ser. No. 840,389 filed Oct. 6, 1977, the contents of which are incorporated by reference.

The compounds of this invention and their preparation are further illustrated by the following examples wherein temperatures are given in degrees centigrade.

EXAMPLE 1

N-[N-(4,6-dimethoxy-1,3,5-triazin-2-yl)-N-methylaminocarbonyl]-2-chlorobenzenesulfonamide To a dry, well-stirred mixture of 1.7 g of 2-methylamino-4,6-dimethoxy-1,3,5-triazine in 25 ml of acetonitrile, at ambient pressure and temperature, was added dropwise 2.2 g of 2-chlorobenzenesulfonyl isocyanate. The resulting mixture was stirred for 18 hours and the precipitated product removed by filtration to yield 2.5 g of white crystals melting at 52°-56°. The product was N-[N-(4,6-dimethoxy-1,3,5-triazin-2-yl)-N-methylaminocarbonyl]-2-chlorobenzenesulfonamide.

EXAMPLE 2

N-[N-(4,6-dimethoxy-1,3,5-triazin-2-yl)-N-methylaminocabonyl]-2-nitrobenzenesulfonamide To a mixture of 1.7 g of 2-methylamino-4,6-dimethoxy-1,3,5-triazine in 50 ml of acetonitrile was added 2.3 g of 2-nitrobenzenesulfonyl isocyanate with stirring. The resultant mixture was stirred at ambient temperature for 72 hours and filtered to afford 1.2 g of a white crystalline solid melting at 184°–186°. The product was N-[N-(4,6-dimethoxy-1,3,5-triazin-2-yl)-N-methylaminocarbonyl]-2-nitrobenzenesulfonamide which showed characteristic infrared absorption peaks at 1710 cm$^{-1}$, 1590 cm$^{-1}$, and 1550 cm$^{-1}$.

By using equivalent amounts of an appropriate 2-alkylamino-1,3,5-triazine and an appropriately substituted benzenesulfonyl isocyanate, the compounds of Formula I set forth in Table I can be prepared by the procedures of Examples 1 or 2.

TABLE (I-A)

| $R_1$ | $R_4$ | $R_5$ | $R_6$ | $R_7$ | $R_8$ |
|---|---|---|---|---|---|
| CH$_3$ | Br | H | H | H | H |
| CH$_3$ | OCH$_3$ | H | H | OCH$_3$ | H |
| CH$_3$ | Cl | H | H | Cl | H |
| CH$_3$ | CH$_3$ | H | H | H | H |
| CH$_3$ | CH$_3$ | H | H | CH$_3$ | H |
| CH$_3$ | H | H | H | H | H |
| CH$_3$ | Cl | H | H | H | Cl |
| CH$_3$ | F | H | H | H | H |
| CH$_3$ | CF$_3$ | H | H | H | H |
| C$_2$H$_5$ | Cl | H | H | H | H |
| C$_2$H$_5$ | NO$_2$ | H | H | Cl | H |
| C$_2$H$_5$ | Cl | H | H | Cl | H |
| C$_2$H$_5$ | CH$_3$ | H | H | H | H |
| n-C$_3$H$_7$ | Cl | H | H | OCH$_3$ | H |
| n-C$_3$H$_7$ | NO$_2$ | H | H | H | H |
| —CH(CH$_3$)$_2$ | Cl | H | H | H | H |
| —CH(CH$_3$)$_2$ | NO$_2$ | H | H | H | H |
| OCH$_3$ | CF$_3$ | H | H | H | H |
| OCH$_3$ | Cl | H | H | H | H |
| OCH$_3$ | CH$_3$ | H | H | H | H |
| OCH$_3$ | Cl | H | H | H | Cl |
| CH$_3$ | OC$_2$H$_5$ | H | H | OC$_2$H$_5$ | H |
| CH$_3$ | C$_2$H$_5$ | H | H | C$_2$H$_5$ | H |
| CH$_3$ | CH(CH$_3$)$_2$ | H | H | H | H |
| CH$_3$ | Br | H | H | Br | H |
| C$_2$H$_5$ | F | H | H | F | H |
| C$_2$H$_5$ | CF$_3$ | H | H | H | H |
| CH$_3$ | CH$_3$ | CH$_3$ | H | CH$_3$ | CH$_3$ |
| CH$_3$ | H | F | H | H | H |
| CH$_3$ | Cl | H | F | H | H |
| CH$_3$ | H | Cl | H | H | H |
| CH$_3$ | SCH$_3$ | H | H | H | H |

TABLE (I-B)

| $R_1$ | $R_4$ | $R_5$ | $R_6$ | $R_7$ | $R_8$ |
|---|---|---|---|---|---|
| CH$_3$ | Cl | H | H | H | H |
| CH$_3$ | NO$_2$ | H | H | H | H |
| CH$_3$ | CH$_3$ | H | H | H | H |
| CH$_3$ | Cl | H | H | Cl | H |
| CH$_3$ | Cl | H | H | H | Cl |
| CH$_3$ | CH$_3$ | H | H | CH$_3$ | H |
| CH$_3$ | H | H | H | H | H |
| CH$_3$ | OCH$_3$ | H | H | OCH$_3$ | H |
| CH$_3$ | F | H | H | H | F |
| C$_2$H$_5$ | NO$_2$ | H | H | H | H |
| —CH(CH$_3$)$_2$ | Cl | H | H | H | H |
| —CH(CH$_3$)$_2$ | Cl | H | H | Cl | H |
| C$_2$H$_5$ | CH$_3$ | H | H | H | H |
| C$_2$H$_5$ | F | H | H | H | H |
| C$_2$H$_5$ | F | H | H | H | F |
| C$_2$H$_5$ | Br | H | H | H | H |
| C$_2$H$_5$ | OC$_2$H$_5$ | H | H | OC$_2$H$_5$ | H |
| OCH$_3$ | Cl | H | H | H | H |
| OCH$_3$ | NO$_2$ | H | H | H | H |
| OCH$_3$ | Cl | H | H | Cl | H |
| OCH$_3$ | F | H | H | H | F |
| CH$_3$ | CH$_3$ | H | H | CH$_3$ | H |
| n-C$_3$H$_7$ | CH$_3$ | H | H | H | H |
| n-C$_3$H$_7$ | OCH$_3$ | H | H | OCH$_3$ | H |
| n-C$_3$H$_7$ | F | H | H | H | H |
| CH$_3$ | SCH$_3$ | H | H | H | H |
| CH$_3$ | Cl | H | F | H | H |
| CH$_3$ | Cl | H | H | OCH$_3$ | H |
| CH$_3$ | n-C$_3$H$_7$O | H | H | n-C$_3$H$_7$O | H |
| CH$_3$ | H | F | H | H | H |
| CH$_3$ | Cl | H | H | NO$_2$ | H |
| CH$_3$ | CH$_3$ | CH$_3$ | H | CH$_3$ | CH$_3$ |
| CH$_3$ | SCH$_2$CH$_3$ | H | H | H | H |

TABLE (I-C)

| $R_1$ | $R_4$ | $R_5$ | $R_6$ | $R_7$ | $R_8$ |
|---|---|---|---|---|---|
| CH$_3$ | Cl | H | H | H | H |
| CH$_3$ | NO$_2$ | H | H | H | H |
| CH$_3$ | CH$_3$ | H | H | H | H |
| CH$_3$ | Cl | H | H | Cl | H |
| CH$_3$ | CH$_3$ | H | H | CH$_3$ | H |
| CH$_3$ | H | H | H | H | H |
| C$_2$H$_5$ | NO$_2$ | H | H | H | H |
| —CH(CH$_3$)$_2$ | Cl | H | H | Cl | H |
| n-C$_3$H$_7$ | Cl | H | H | H | H |
| CH$_3$ | OCH$_3$ | H | H | H | H |
| CH$_3$ | OCH$_3$ | H | H | OCH$_3$ | H |
| C$_2$H$_5$ | SCH$_3$ | H | H | H | H |
| C$_2$H$_5$ | F | H | H | H | H |
| C$_2$H$_5$ | Cl | H | H | Cl | H |
| C$_2$H$_5$ | Br | H | H | H | H |
| C$_2$H$_5$ | CF$_3$ | H | H | H | H |
| n-C$_3$H$_7$ | CH$_3$ | H | H | H | H |
| n-C$_3$H$_7$ | NO$_2$ | H | H | H | H |
| CH$_3$ | CH$_3$ | CH$_3$ | H | CH$_3$ | CH$_3$ |
| CH$_3$ | C$_2$H$_5$ | H | H | H | H |
| CH$_3$ | OC$_2$H$_5$ | H | H | OC$_2$H$_5$ | H |
| CH$_3$ | n-C$_4$H$_9$O | H | H | n-C$_4$H$_9$O | H |
| CH$_3$ | Cl | H | H | OCH$_3$ | H |
| CH$_3$ | H | F | H | H | H |
| CH$_3$ | SC$_2$H$_5$ | H | H | H | H |
| OCH$_3$ | Cl | H | H | H | H |

TABLE (I-C)-continued $R_6$, $R_7$, $R_8$ on benzene ring; $R_5$, $R_4$ also on ring; $-SO_2NHC(O)N(R_1)-$ linked to pyrimidine with 4,6-di-CH$_3$ substituents.

| $R_1$ | $R_4$ | $R_5$ | $R_6$ | $R_7$ | $R_8$ |
|---|---|---|---|---|---|
| OCH$_3$ | F | H | H | H | H |
| OCH$_3$ | F | H | H | H | F |
| OCH$_3$ | CH$_3$ | H | H | H | H |
| OCH$_3$ | Cl | H | H | Cl | H |
| CH$_3$ | F | H | F | H | F |
| CH$_3$ | Br | H | H | H | H |
| CH$_3$ | Cl | Cl | H | H | H |
| CH$_3$ | i-C$_3$H$_7$O | H | H | i-C$_3$H$_7$O | H |

TABLE (I-D)

Structure: benzenesulfonylurea linked to pyrimidine with X and CH$_3$ substituents.

| $R_1$ | $R_4$ | $R_5$ | $R_6$ | $R_7$ | $R_8$ | X |
|---|---|---|---|---|---|---|
| CH$_3$ | Cl | H | H | H | H | C$_2$H$_5$ |
| CH$_3$ | NO$_2$ | H | H | H | H | C$_2$H$_5$ |
| CH$_3$ | Cl | H | H | N | H | OC$_2$H$_5$ |
| CH$_3$ | CH$_3$ | H | H | CH$_3$ | H | CF$_3$ |
| CH$_3$ | F | H | H | H | H | SCH$_3$ |
| CH$_3$ | Cl | H | H | H | Cl | CH$_2$OCH$_3$ |
| C$_2$H$_5$ | NO$_2$ | H | H | H | H | OC$_2$H$_5$ |
| C$_2$H$_5$ | Cl | H | H | H | H | C$_2$H$_5$ |
| CH$_3$ | NO$_2$ | H | H | H | H | Cl |
| CH$_3$ | Cl | H | H | Cl | H | Cl |
| CH$_3$ | CH$_3$ | H | H | H | H | OCH$_2$CH$_2$OCH$_3$ |
| CH$_3$ | OCH$_3$ | H | H | OCH$_3$ | H | n-C$_3$H$_7$O |
| CH$_3$ | Br | H | H | H | H | CF$_3$ |
| CH$_3$ | H | F | H | H | H | OC$_2$H$_5$ |
| C$_2$H$_5$ | NO$_2$ | H | H | H | H | SCH$_3$ |
| C$_2$H$_5$ | OC$_2$H$_5$ | H | H | OC$_2$H$_5$ | H | OC$_2$H$_5$ |
| C$_2$H$_5$ | Br | H | H | H | H | OC$_2$H$_5$ |
| C$_2$H$_5$ | Cl | H | H | Cl | H | C$_2$H$_5$ |
| n-C$_3$H$_7$ | Cl | H | H | H | H | CH$_2$OCH$_3$ |
| n C$_3$H$_7$ | CH$_3$ | H | H | H | H | SCH$_3$ |
| i C$_3$H$_7$ | F | H | H | H | F | OCH$_2$CH$_2$OCH$_3$ |
| i-C$_3$H$_7$ | CF$_3$ | H | H | H | H | OC$_2$H$_5$ |
| OCH$_3$ | F | H | H | H | H | C$_2$H$_5$ |

TABLE (I-E)

Structure: benzenesulfonylurea linked to pyrimidine with X and OCH$_3$ substituents.

| $R_1$ | $R_4$ | $R_5$ | $R_6$ | $R_7$ | $R_8$ | X |
|---|---|---|---|---|---|---|
| CH$_3$ | Cl | H | H | H | H | C$_2$H$_5$ |
| CH$_3$ | NO$_2$ | H | H | H | H | C$_2$H$_5$ |
| CH$_3$ | Cl | H | H | H | Cl | OC$_2$H$_5$ |
| CH$_3$ | OCH$_3$ | H | H | OCH$_3$ | H | OC$_2$H$_5$ |
| CH$_3$ | Cl | H | H | H | H | Cl |
| CH$_3$ | NO$_2$ | H | H | H | H | Cl |
| CH$_3$ | Cl | H | H | H | Cl | CH$_2$OCH$_3$ |
| CH$_3$ | F | H | H | H | H | SCH$_3$ |
| C$_2$H$_5$ | NO$_2$ | H | H | H | H | OC$_2$H$_5$ |
| C$_2$H$_5$ | Cl | H | H | H | H | OC$_2$H$_5$ |
| —CH(CH$_3$)$_2$ | CH$_3$ | H | H | H | H | OC$_2$H$_5$ |
| —CH(CH$_3$)$_2$ | F | H | H | H | F | OCH$_2$CH$_2$OCH$_3$ |
| C$_2$H$_5$ | Br | H | H | H | H | C$_2$H$_5$ |
| C$_2$H$_5$ | OCH$_3$ | H | H | H | H | n-C$_3$H$_7$O |
| C$_2$H$_5$ | CH$_3$ | H | H | CH$_3$ | H | C$_2$H$_5$ |
| n-C$_3$H$_7$ | Cl | H | H | Cl | H | CF$_3$ |
| n-C$_3$H$_7$ | OCH$_3$ | H | H | OCH$_3$ | H | Cl |
| n-C$_3$H$_7$ | F | H | H | F | H | OC$_2$H$_5$ |
| CH$_3$ | H | H | H | H | H | CH$_2$OCH$_3$ |
| CH$_3$ | CH$_3$ | H | H | NO$_2$ | H | SCH$_3$ |
| CH$_3$ | CF$_3$ | H | H | H | H | OCH$_2$CH$_2$OCH$_3$ |
| CH$_3$ | OC$_2$H$_5$ | H | H | OC$_2$H$_5$ | H | C$_2$H$_5$ |
| CH$_3$ | SCH$_2$CH$_3$ | H | H | H | H | OC$_2$H$_5$ |
| OCH$_3$ | F | H | H | H | H | C$_2$H$_5$ |

EXAMPLE 3

N-[N-(4-methoxy-6-methylpyrimidin-2-yl)-N-methylaminocarbonyl]-2,5-dichlorobenzenesulfonamide To a stirred mixture of 0.8 g of 2-methylamino-4-methoxy-6-methylpyrimidine in 25 ml of acetonitrile containing a few crystals of 1,4-diazabicyclo[2.2.2]octane was added dropwise 1.3 g of 2,5-dichlorobenzenesulfonyl isocyanate. The mixture was stirred for 16 hours and the resultant solid was filtered to afford 1.2 g of N-[N-(4-methoxy-6-methylpyrimidine-2-yl)-N-methylaminocarbonyl]-2,5-dichlorobenzenesulfonamide melting at 182°–185°. Infrared absorption spectrum showed peaks at 1690 cm$^{-1}$, 1590 cm$^{-1}$, and 1550 cm$^{-1}$ which are typical for this type of compound.

EXAMPLE 4

N-[N-(4-methoxy-6-methylpyrimidin-2-yl)-N-methylaminocarbonyl]-2,6-dichlorobenzenesulfonamide To 0.8 g of 4-methoxy-6-methyl-2-methylaminopyrimidine in 25 ml of dry acetonitrile containing a few crystals of 1,4-diazabicyclo[2.2.2]octane was added 1.3 g of 2,6-dichlorobenzenesulfonyl isocyanate. The mixture was stirred at ambient temperature for 16 hours and the resultant solution was evaporated leaving a white solid. Trituration with 1-chlorobutane followed by filtration afforded 0.5 g of N-[N-(4-methoxy-6-methylpyrimidine-2-yl)-N-methylaminocarbonyl]-2,6-dichlorobenzenesulfonamide melting at 170°–171°. Infrared absorption peaks were observed at 1700 cm$^{-1}$, 1600 cm$^{-1}$, and 1570 cm$^{-1}$.

By using equivalent amounts of an appropriate 2-alkylaminopyrimidine and an appropriately substituted benzenesulfonyl isocyanate, the compounds of Formula I set forth in Table II can be prepared by the procedures of Examples 3 and 4.

TABLE (II-A)

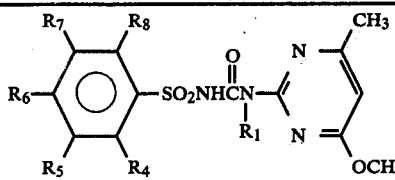

| R1 | R4 | R5 | R6 | R7 | R8 | m.p. |
|---|---|---|---|---|---|---|
| CH3 | Cl | H | H | H | H | 168–170° |
| CH3 | CH3 | H | H | H | H | |
| CH3 | NO2 | H | H | H | H | |
| CH3 | F | H | H | H | H | |
| CH3 | CH3 | H | H | CH3 | H | |
| CH3 | OCH3 | H | H | OCH3 | H | |
| CH3 | CF3 | H | H | H | H | |
| CH3 | H | H | H | H | H | |
| CH3 | OCH3 | H | H | Cl | H | |
| C2H5 | Cl | H | H | H | H | |
| C2H5 | Cl | H | H | Cl | H | |
| —CH(CH3)2 | NO2 | H | H | H | H | |
| n-C3H7 | Cl | H | H | H | Cl | |
| OCH3 | NO2 | H | H | H | H | |
| OCH3 | CH3 | H | H | H | H | |
| OCH3 | CF3 | H | H | H | H | |
| OCH3 | Cl | H | H | NO2 | H | |
| OCH3 | F | H | H | F | H | |
| n-C3H7 | F | H | H | H | F | |
| —CH(CH3)2 | CF3 | H | H | H | H | |
| —CH(CH3)2 | Cl | H | H | OCH3 | H | |
| n-C3H7 | CH3 | H | H | H | H | |
| C2H5 | OCH3 | H | H | Cl | H | |
| C2H5 | H | F | H | H | H | |
| C2H5 | CH3 | CH3 | H | CH3 | CH3 | |
| C2H5 | —CH(CH3)2 | H | H | H | H | |
| C2H5 | OC2H5 | H | H | OC2H5 | H | |
| CH3 | SCH3 | H | H | H | H | |
| CH3 | SC2H5 | H | H | H | H | |
| CH3 | —C3H7O | H | H | n-C3H7O | H | |
| CH3 | H | Cl | H | H | H | |
| CH3 | C2H5 | H | H | C2H5 | H | |
| CH3 | Br | H | H | Br | H | |
| CH3 | Cl | H | F | H | H | |
| CH3 | Cl | Cl | H | Cl | Cl | |
| CH3 | CH3 | H | H | Cl | H | |

TABLE (II-B)

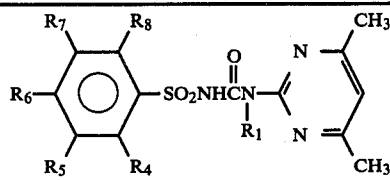

| R1 | R4 | R5 | R6 | R7 | R8 | m.p. |
|---|---|---|---|---|---|---|
| CH3 | H | H | H | H | H | 146–147 |
| CH3 | Cl | H | H | H | H | |
| CH3 | NO2 | H | H | H | H | |
| CH3 | Cl | H | H | Cl | H | |
| CH3 | Cl | H | H | H | Cl | |
| CH3 | CH3 | H | H | H | H | |
| CH3 | CH3 | H | H | CH3 | H | |
| CH3 | OCH3 | H | H | OCH3 | H | |
| CH3 | F | H | H | H | H | |
| CH3 | OCH3 | H | H | Cl | H | |
| CH3 | CF3 | H | H | H | H | |
| C2H5 | Cl | H | H | H | H | |
| C2H5 | Cl | H | H | Cl | H | |
| C2H5 | H | F | H | H | H | |
| C2H5 | CH3 | CH3 | H | CH3 | CH3 | |
| C2H5 | OC2H5 | H | H | OC2H5 | H | |
| C2H5 | OCH3 | H | H | Cl | H | |
| C2H5 | Br | H | H | H | H | |
| n-C3H7 | CH3 | H | H | H | H | |
| n-C3H7 | F | H | H | H | F | |
| n-C3H7 | Cl | H | H | H | Cl | |
| —CH(CH3)2 | CF3 | H | H | H | H | |

TABLE (II-B)-continued

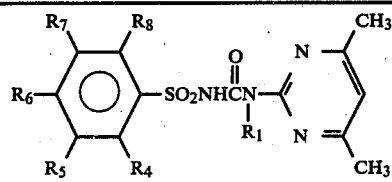

| R1 | R4 | R5 | R6 | R7 | R8 | m.p. |
|---|---|---|---|---|---|---|
| —CH(CH3)2 | Cl | H | H | OCH3 | H | |
| —CH(CH3)2 | NO2 | H | H | H | H | |
| OCH3 | NO2 | H | H | H | H | |
| OCH3 | CH3 | H | H | H | H | |
| OCH3 | CF3 | H | H | H | H | |
| OCH3 | Cl | H | H | NO2 | H | |
| OCH3 | F | H | H | F | H | |
| CH3 | SCH3 | H | H | H | H | |
| CH3 | SC2H5 | H | H | H | H | |
| CH3 | n-C3H7O | H | H | n-C3H7O | H | |
| CH3 | H | Cl | H | H | H | |
| CH3 | C2H5 | H | H | C2H5 | H | |
| CH3 | Br | H | H | Br | H | |
| CH3 | Cl | H | F | H | H | |
| CH3 | Cl | Cl | H | Cl | Cl | |
| CH3 | CH3 | H | H | Cl | H | |

TABLE (II-C)

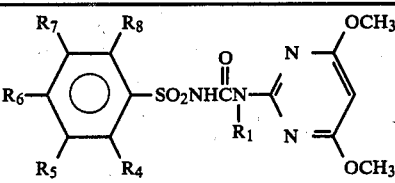

| R1 | R4 | R5 | R6 | R7 | R8 |
|---|---|---|---|---|---|
| CH3 | Cl | H | H | H | H |
| CH3 | Cl | H | H | Cl | H |
| CH3 | Cl | H | H | H | Cl |
| CH3 | NO2 | H | H | H | H |
| CH3 | CH3 | H | H | H | H |
| CH3 | CH3 | H | H | CH3 | H |
| CH3 | OCH3 | H | H | OCH3 | H |
| CH3 | F | H | H | H | H |
| CH3 | OCH3 | H | H | Cl | H |
| C2H5 | Cl | H | H | H | H |
| C2H5 | H | F | H | H | H |
| —CH(CH3)2 | CF3 | H | H | H | H |
| —CH(CH3)2 | Cl | H | H | OCH3 | H |
| n-C3H7 | F | H | H | H | F |
| n-C3H7 | Cl | H | H | H | Cl |
| n-C3H7 | CH3 | H | H | H | H |
| C2H5 | H | Cl | H | H | H |
| C2H5 | CH3 | CH3 | H | CH3 | CH3 |
| C2H5 | OC2H5 | H | H | OC2H5 | H |
| C2H5 | OCH3 | H | H | Cl | H |
| C2H5 | Br | H | H | H | H |
| —CH(CH3)2 | NO2 | H | H | Cl | H |
| OCH3 | NO2 | H | H | H | H |
| OCH3 | CH3 | H | H | H | H |
| OCH3 | CF3 | H | H | H | H |
| OCH3 | Cl | H | H | NO2 | H |
| OCH3 | F | H | H | F | H |
| CH3 | SCH3 | H | H | H | H |
| CH3 | SC2H5 | H | H | H | H |
| CH3 | n-C3H7O | H | H | n-C3H7O | H |
| CH3 | H | Cl | H | H | H |
| CH3 | H | H | F | H | H |
| CH3 | C2H5 | H | H | C2H5 | H |
| CH3 | Br | H | H | Br | H |
| CH3 | Cl | H | F | H | H |
| CH3 | Cl | Cl | H | Cl | Cl |
| CH3 | CH3 | H | H | Cl | H |

TABLE (II-D)

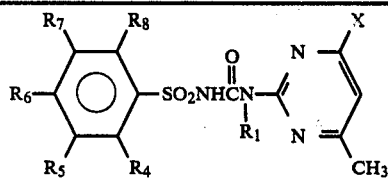

| R1 | R4 | R5 | R6 | R7 | R8 | X |
|---|---|---|---|---|---|---|
| CH3 | Cl | H | H | H | H | C2H5 |
| CH3 | NO2 | H | H | H | H | C2H5 |
| CH3 | Cl | H | H | Cl | H | OC2H5 |
| CH3 | CH3 | H | H | CH3 | H | CF3 |
| CH3 | F | H | H | H | H | SCH3 |
| CH3 | Cl | H | H | H | Cl | CH2OCH3 |
| CH3 | NO2 | H | H | H | H | Cl |
| CH3 | Cl | H | H | Cl | H | Cl |
| CH3 | CH3 | H | H | H | H | OCH2CH2OCH3 |
| CH3 | Br | H | H | H | H | n-C3H7O |
| CH3 | H | F | H | H | H | CF3 |
| CH3 | OCH3 | H | H | OCH3 | H | OC2H5 |
| C2H5 | NO2 | H | H | H | H | OC2H5 |
| C2H5 | Cl | H | H | H | H | C2H5 |
| C2H5 | CH3 | H | H | H | H | SCH3 |
| C2H5 | OC2H5 | H | H | OC2H5 | H | OC2H5 |
| C2H5 | Cl | H | H | Cl | H | CF3 |
| n-C3H7 | Cl | H | H | H | H | CH2OCH3 |
| n-C3H7 | CH3 | H | H | Cl | H | SCH3 |
| —CH(CH3)2 | F | H | H | H | F | OCH2CH2OCH3 |
| —CH(CH3)2 | CF3 | H | H | H | H | OC2H5 |
| OCH3 | F | H | H | H | H | C2H5 |

TABLE (II-E)

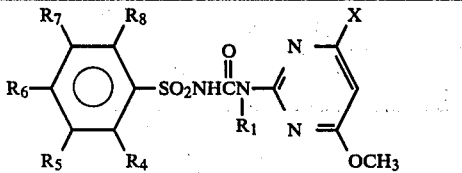

| R1 | R4 | R5 | R6 | R7 | R8 | X |
|---|---|---|---|---|---|---|
| CH3 | Cl | H | H | H | H | C2H5 |
| CH3 | NO2 | H | H | H | H | C2H5 |
| CH3 | Cl | H | H | H | Cl | OC2H5 |
| CH3 | OCH3 | H | H | OCH3 | H | OC2H5 |
| CH3 | Cl | H | H | H | H | Cl |
| CH3 | NO2 | H | H | H | H | Cl |
| CH3 | F | H | H | H | F | CH2OCH3 |
| CH3 | F | H | H | H | H | SCH3 |
| CH3 | H | H | H | H | H | CH2OCH3 |
| CH3 | CH3 | H | H | NO2 | H | SCH3 |
| CH3 | CF3 | H | H | H | H | OCH2CH2OCH3 |
| CH3 | OC2H5 | H | H | OC2H5 | H | C2H5 |
| CH3 | SC2H5 | H | H | H | H | OC2H5 |
| C2H5 | NO2 | H | H | H | H | (CH3)2CHO |
| C2H5 | Cl | H | H | H | H | OC2H5 |
| C2H5 | Br | H | H | H | H | C2H5 |
| C2H5 | OCH3 | H | H | H | H | n-C3H7O |
| C2H5 | CH3 | H | H | CH3 | H | CF3 |
| n-C3H7 | Cl | H | H | Cl | H | CF3 |
| n-C3H7 | OCH3 | H | H | OCH3 | H | Cl |
| n-C3H7 | F | H | H | F | H | OC2H5 |
| —CH(CH3)2 | CH3 | H | H | H | H | OC2H5 |
| —CH3(CH3)2 | F | H | H | H | F | OCH2CH2OCH3 |
| OCH3 | F | H | H | H | H | C2H5 |

EXAMPLE 5

N-[N-(4-methoxy-6-methylpyrimidin-2-yl)-N-methylaminocarbonyl]-2-thiophenesulfonamide To a mixture, 1.5 g of 2-methylamino-4-methoxy-6-methylpyrimidine in 50 ml of acetonitrile is added 1.9 g of 2-thiophenesulfonyl isocyanate. Filtration affords N-[N-(4-methoxy-6-methylpyrimidin-2-yl)-N-methylaminocarbonyl]-2-thiophene sulfonamide.

By using equivalent amounts of an appropriate 2-alkylaminopyrimidine or 2-alkylamino-1,3,5-triazine and 2-thiophenesulfonyl isocyanate, the compounds of Formula I set forth in Table III can be prepared by the procedure of Example 5.

TABLE III

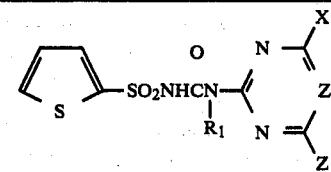

| R1 | Z | X | Y |
|---|---|---|---|
| CH3 | CH | CH3 | CH3 |
| CH3 | CH | OCH3 | CH3 |
| CH3 | CH | OCH3 | OCH3 |
| CH3 | CH | CH2CH3 | OCH3 |
| CH3 | CH | OCH2CH3 | OCH3 |
| CH3 | CH | CF3 | CH3 |
| CH3 | N | CH3 | CH3 |
| CH3 | N | OCH3 | CH3 |
| CH3 | N | OCH3 | OCH |
| CH3 | N | OCH2CH3 | OCH3 |
| CH3 | N | Cl | OCH3 |
| CH3 | N | SCH3 | OCH3 |
| C2H5 | CH | OCH3 | CH3 |
| C2H5 | CH | CH3 | CH3 |
| —CH(CH3)2 | CH | OCH3 | CH3 |
| n-C3H7 | CH | CH3 | CH3 |
| C2H5 | N | OCH3 | OCH3 |
| C2H5 | N | CH3 | CH3 |
| C2H5 | N | CH3 | OCH3 |
| n-C3H7 | N | OCH3 | OCH3 |
| —CH(CH3)2 | N | OCH3 | OCH3 |
| n-C3H7 | N | CH3 | CH3 |
| CH3 | CH | Cl | CH3 |
| CH3 | CH | Cl | OCH3 |
| C2H5 | CH | n-C3H7O | CH3 |
| C2H5 | CH | OCH(CH3)2 | OCH3 |
| C2H5 | CH | SCH3 | CH3 |
| CH3 | N | n-C3H7O | OCH3 |
| CH3 | N | OCH2CH2OCH3 | OCH3 |
| CH3 | N | C2H5 | CH3 |
| CH3 | N | OCH(CH3)2 | CH3 |

EXAMPLE 6

N-[N-(4,6-Dimethoxy-1,3,5-triazin-2-yl)-N-aminocarbonyl]-2,5-dimethoxy-N-methylbenzenesulfonamide An equivalent amount of sodium hydride (50% mineral oil dispersion) is added to a solution of N-[(4,6-dimethoxy-1,3,5-triazin-2-yl)aminocarbonyl]2,5-dimethoxybenzenesulfonamide in dimethylformamide under a nitrogen atmosphere. After hydrogen evolution ceases, an equivalent amount of dimethyl sulfate is added. After stirring for 2–18 hours, the reaction mixture is poured into a large volume of water. The resulting precipitate is filtered to yield N-[N-(4,6-dimethoxy-1,3,5-triazin-2-yl)-N-aminocarbonyl]-2,5-dimethoxy-N-methylbenzenesulfonamide.

EXAMPLE 7

N-[N-(4-Methoxy-6-methylpyrimidin-2-yl)-N-methylaminocarbonyl]2,5-dichloro-N-methylbenzenesulfonamide To 3.0 g of N-[(2,5-dichlorophenyl)sulfonyl]-N-methylcarbamyl chloride in 50 ml of tetrahydrofuran containing 1.0 g of triethylamine is added 1.5 g of 2- methylamino-4-methoxy-6-methylpyrimidine. After stirring at reflux for several hours, the precipitated salts are filtered off and the filtrate is concentrated to yield N-[N-(4-methoxy-6-methylpyrimidin-2-yl)-N-methylaminocarbonyl]2,5-dichloro-N-methylbenzenesulfonamide.

By using an appropriate N-(1,3,5-triazin-2-yl)-N-aminocarbonylbenzenesulfonamide or N-pyrimidin-2-yl-N-aminocarbonylbenzenesulfonamide, the following compounds of Formula I as set forth in Table IV can be prepared by the procedure of Example 6. Alternatively, by using an appopriately substituted sulfonyl-N-alkylbenzene carbamyl chloride and an appropriate 2-aminopyrimidine or 2-amino-1,3,5-triazine, the same compounds of Formula I can be prepared by the procedure of Example 7.

TABLE IV-A

| $R_1$ | $R_2$ | $R_4$ | $R_5$ | $R_6$ | $R_7$ | $R_8$ |
|---|---|---|---|---|---|---|
| H | CH$_3$ | OCH$_3$ | H | H | OCH$_3$ | H |
| H | CH$_3$ | Cl | H | H | H | H |
| H | CH$_3$ | NO$_2$ | H | H | H | H |
| H | CH$_3$ | Cl | H | H | Cl | H |
| H | CH$_3$ | CH$_3$ | H | H | H | H |
| H | CH$_3$ | Cl | H | F | H | H |
| H | CH$_3$ | H | H | H | H | H |
| H | CH$_3$ | CH$_3$ | H | H | CH$_3$ | H |
| H | CH$_3$ | OC$_2$H$_5$ | H | H | OC$_2$H$_5$ | H |
| CH$_3$ | CH$_3$ | Cl | H | H | H | H |
| CH$_3$ | CH$_3$ | NO$_2$ | H | H | CH$_3$ | H |
| CH$_3$ | CH$_3$ | CH$_3$ | H | H | NO$_2$ | H |
| CH$_3$ | CH$_3$ | Cl | H | H | Cl | H |
| CH$_3$ | CH$_3$ | CH$_3$ | H | H | Cl | H |
| CH$_3$ | CH$_3$ | CH$_3$ | CH$_3$ | H | CH$_3$ | CH$_3$ |
| CH$_3$ | CH$_3$ | OCH$_3$ | H | H | OCH$_3$ | H |
| CH$_3$ | CH$_3$ | F | H | H | F | H |
| C$_2$H$_5$ | CH$_3$ | NO$_2$ | H | H | H | H |
| C$_2$H$_5$ | CH$_3$ | Cl | H | H | H | Cl |
| H | C$_2$H$_5$ | F | H | H | H | H |
| H | C$_2$H$_5$ | CF$_3$ | H | H | H | H |
| H | C$_2$H$_5$ | OCH$_3$ | H | H | OCH$_3$ | H |
| CH$_3$ | C$_2$H$_5$ | Cl | H | H | H | H |
| CH$_3$ | C$_2$H$_5$ | NO$_2$ | H | H | Cl | H |
| CH$_3$ | C$_2$H$_5$ | CH$_3$ | CH$_3$ | H | CH$_3$ | CH$_3$ |
| n-C$_3$H$_7$ | C$_2$H$_5$ | F | H | H | H | F |
| n-C$_3$H$_7$ | C$_2$H$_5$ | Br | H | H | H | H |
| n-C$_3$H$_7$ | C$_2$H$_5$ | CF$_3$ | H | H | H | H |
| CH(CH$_3$)$_2$ | CH$_3$ | Cl | H | H | Cl | H |
| CH$_3$ | n-C$_3$H$_7$ | Cl | H | H | Cl | H |
| H | n-C$_3$H$_7$ | NO$_2$ | H | H | H | H |
| H | CH(CH$_3$)$_2$ | CF$_3$ | H | H | H | H |
| CH$_3$ | CH(CH$_3$)$_2$ | Cl | H | H | H | H |
| OCH$_3$ | CH$_3$ | Cl | H | H | H | H |
| OCH$_3$ | CH$_3$ | CH$_3$ | H | H | H | H |

TABLE IV-B

| $R_1$ | $R_2$ | $R_4$ | $R_5$ | $R_6$ | $R_7$ | $R_8$ |
|---|---|---|---|---|---|---|
| H | CH$_3$ | OCH$_3$ | H | H | OCH$_3$ | H |
| H | CH$_3$ | Cl | H | H | H | H |

TABLE IV-B-continued

| $R_1$ | $R_2$ | $R_4$ | $R_5$ | $R_6$ | $R_7$ | $R_8$ |
|---|---|---|---|---|---|---|
| H | CH$_3$ | NO$_2$ | H | H | H | H |
| H | CH$_3$ | Cl | H | H | Cl | H |
| H | CH$_3$ | CH$_3$ | H | H | H | H |
| H | CH$_3$ | Cl | H | F | H | H |
| H | CH$_3$ | H | H | H | H | H |
| H | CH$_3$ | CH$_3$ | H | H | CH$_3$ | H |
| H | CH$_3$ | OC$_2$H$_5$ | H | H | OC$_2$H$_5$ | H |
| CH$_3$ | CH$_3$ | NO$_2$ | H | H | CH$_3$ | H |
| CH$_3$ | CH$_3$ | Cl | H | H | Cl | H |
| CH$_3$ | CH$_3$ | CH$_3$ | H | H | Cl | H |
| CH$_3$ | CH$_3$ | CH$_3$ | CH$_3$ | H | CH$_3$ | CH$_3$ |
| CH$_3$ | CH$_3$ | OCH$_3$ | H | H | H | H |
| CH$_3$ | CH$_3$ | F | H | H | F | H |
| C$_2$H$_5$ | CH$_3$ | NO$_2$ | H | H | H | H |
| C$_2$H$_5$ | CH$_3$ | Cl | H | H | H | Cl |
| H | C$_2$H$_5$ | F | H | H | H | H |
| H | C$_2$H$_5$ | CF$_3$ | H | H | H | H |
| H | C$_2$H$_5$ | OC$_2$H$_5$ | H | H | H | H |
| CH$_3$ | C$_2$H$_5$ | OCH$_3$ | H | H | OCH$_3$ | H |
| CH$_3$ | C$_2$H$_5$ | CH$_3$ | H | H | NO$_2$ | H |
| n-C$_3$H$_7$ | C$_2$H$_5$ | F | H | H | H | F |
| n-C$_3$H$_7$ | C$_2$H$_5$ | Br | H | H | H | H |
| CH(CH$_3$)$_2$ | C$_2$H$_5$ | CF$_3$ | H | H | H | H |
| CH(CH$_3$)$_2$ | CH$_3$ | Cl | H | H | OCH$_3$ | H |
| n-C$_3$H$_7$ | CH$_3$ | F | H | H | F | H |
| CH$_3$ | n-C$_3$H$_7$ | Cl | H | H | Cl | H |
| H | n-C$_3$H$_7$ | NO$_2$ | H | H | H | H |
| H | CH(CH$_3$)$_2$ | CF$_3$ | H | H | H | H |
| CH$_3$ | CH(CH$_3$)$_2$ | Cl | H | H | H | H |
| OCH$_3$ | CH$_3$ | F | H | H | H | F |
| OCH$_3$ | CH$_3$ | CH$_3$ | H | H | H | H |

TABLE IV-C

| $R_1$ | $R_2$ | $R_4$ | $R_5$ | $R_6$ | $R_7$ | $R_8$ |
|---|---|---|---|---|---|---|
| H | CH$_3$ | OCH$_3$ | H | H | OCH$_3$ | H |
| H | CH$_3$ | Cl | H | H | H | H |
| H | CH$_3$ | NO$_2$ | H | H | H | H |
| H | CH$_3$ | Cl | H | H | Cl | H |
| H | CH$_3$ | CH$_3$ | H | H | H | H |
| H | CH$_3$ | Cl | H | F | H | H |
| H | CH$_3$ | H | H | H | H | H |
| H | CH$_3$ | CH$_3$ | H | H | CH$_3$ | H |
| H | CH$_3$ | OC$_2$H$_5$ | H | H | OC$_2$H$_5$ | H |
| CH$_3$ | CH$_3$ | NO$_2$ | H | H | CH$_3$ | H |
| CH$_3$ | CH$_3$ | Cl | H | H | Cl | H |
| CH$_3$ | CH$_3$ | CH$_3$ | H | H | Cl | H |
| CH$_3$ | CH$_3$ | CH$_3$ | CH$_3$ | H | CH$_3$ | CH$_3$ |
| CH$_3$ | CH$_3$ | OCH$_3$ | H | H | H | H |
| CH$_3$ | CH$_3$ | F | H | H | F | H |
| C$_2$H$_5$ | CH$_3$ | NO$_2$ | H | H | H | H |
| C$_2$H$_5$ | CH$_3$ | Cl | H | H | H | Cl |
| H | C$_2$H$_5$ | F | H | H | H | H |
| H | C$_2$H$_5$ | CF$_3$ | H | H | H | H |
| H | C$_2$H$_5$ | OC$_2$H$_5$ | H | H | H | H |
| CH$_3$ | C$_2$H$_5$ | OCH$_3$ | H | H | OCH$_3$ | H |
| CH$_3$ | C$_2$H$_5$ | CH$_3$ | H | H | NO$_2$ | H |
| n-C$_3$H$_7$ | C$_2$H$_5$ | F | H | H | H | F |
| n-C$_3$H$_7$ | C$_2$H$_5$ | Br | H | H | H | H |
| CH(CH$_3$)$_2$ | C$_2$H$_5$ | CF$_3$ | H | H | H | H |
| CH(CH$_3$)$_2$ | CH$_3$ | Cl | H | H | OCH$_3$ | H |

TABLE IV-C-continued structure: R7, R8, R6, R5, R4 on benzene; SO2N(R2)-C(=O)-N(R1)-C(=N-)(N=) triazine with two CH3 groups

| R1 | R2 | R4 | R5 | R6 | R7 | R8 |
|---|---|---|---|---|---|---|
| n-C3H7 | CH3 | F | H | H | F | H |
| OCH3 | CH3 | CH3 | H | H | H | H |
| OCH3 | CH3 | Cl | H | H | H | H |
| CH3 | n-C3H7 | Cl | H | H | Cl | H |
| H | n-C3H7 | NO2 | H | H | H | H |
| H | CH(CH3)2 | CF3 | H | H | H | H |
| CH3 | CH(CH3)2 | Cl | H | H | H | H |

TABLE IV-D structure: phenyl(R4-R8)-SO2N(R2)-C(=O)-N(R1)-triazine with X, N, CH3 substituents

| R1 | R2 | R4 | R5 | R6 | R7 | R8 | X |
|---|---|---|---|---|---|---|---|
| H | CH3 | Cl | H | H | H | H | C2H5 |
| H | CH3 | NO2 | H | H | H | H | C2H5 |
| H | CH3 | CH3 | H | H | H | H | C2H5 |
| H | CH3 | Cl | H | H | NO2 | H | OC2H5 |
| H | CH3 | NO2 | H | H | CH3 | H | OC2H5 |
| H | CH3 | CH3 | H | H | H | H | n-C3H7O |
| H | CH3 | OCH3 | H | H | H | H | SCH3 |
| H | C2H5 | Cl | H | H | Cl | H | CH2OCH3 |
| CH3 | CH3 | F | H | H | H | H | C2H5 |
| CH3 | CH3 | CF3 | H | H | H | H | C2H5 |
| CH3 | CH3 | CH3 | H | H | CH3 | H | OC2H5 |
| CH3 | CH3 | CH3 | H | H | NO2 | H | OC2H5 |
| CH3 | CH3 | H | H | H | H | H | CF3 |
| C2H5 | CH3 | F | H | H | F | H | OCH2CH2OCH3 |
| C2H5 | CH3 | Br | H | H | H | H | n-C3H7O |
| C2H5 | CH3 | OCH3 | H | H | OCH3 | H | Cl |
| CH3 | C2H5 | Cl | H | F | H | H | OC2H5 |
| C2H5 | C2H5 | NO2 | H | H | CH3 | H | CH2OCH3 |
| n-C3H7 | CH3 | Cl | H | H | H | Cl | SCH3 |
| n-C3H7 | CH3 | OCH3 | H | H | Cl | H | OC2H5 |
| OCH3 | CH3 | F | H | H | H | F | OCH(CH3)2 |
| CH(CH3)2 | C2H5 | Cl | H | H | NO2 | H | C2H5 |
| CH3 | n-C3H7 | Cl | H | H | Cl | H | OC2H5 |
| H | n-C3H7 | NO2 | H | H | H | H | OC2H5 |
| H | CH(CH3)2 | CF3 | H | H | H | H | OC2H5 |
| CH3 | CH(CH3)2 | Cl | H | H | H | H | OC2H5 |

TABLE IV-E structure: phenyl(R4-R8)-SO2N(R2)-C(=O)-N(R1)-triazine with X, N, OCH3

| R1 | R2 | R4 | R5 | R6 | R7 | R8 | X |
|---|---|---|---|---|---|---|---|
| H | CH3 | Cl | H | H | H | H | C2H5 |
| H | CH3 | NO2 | H | H | H | H | C2H5 |
| H | CH3 | CH3 | H | H | H | H | C2H5 |
| H | CH3 | Cl | H | H | NO2 | H | OC2H5 |
| H | CH3 | NO2 | H | H | CH3 | H | OC2H5 |
| H | CH3 | CH3 | H | H | H | H | n-C3H7O |
| H | CH3 | OCH3 | H | H | H | H | SCH3 |
| H | C2H5 | Cl | H | H | Cl | H | CH2OCH3 |
| CH3 | CH3 | F | H | H | H | H | C2H5 |
| CH3 | CH3 | CF3 | H | H | H | H | C2H5 |
| CH3 | CH3 | CH3 | H | H | CH3 | H | OC2H5 |
| CH3 | CH3 | CH3 | H | H | NO2 | H | OC2H5 |
| CH3 | CH3 | H | H | H | H | H | CF3 |
| C2H5 | CH3 | F | H | H | F | H | OCH2CH2OCH3 |
| C2H5 | CH3 | Br | H | H | H | H | n-C3H7O |
| C2H5 | CH3 | OCH3 | H | H | OCH3 | H | Cl |
| CH3 | C2H5 | Cl | H | F | H | H | OC2H5 |
| C2H5 | C2H5 | NO2 | H | H | CH3 | H | CH2OCH3 |
| n-C3H7 | CH3 | Cl | H | H | H | Cl | SCH3 |
| n-C3H7 | CH3 | OCH3 | H | H | Cl | H | OC2H5 |

TABLE IV-E-continued

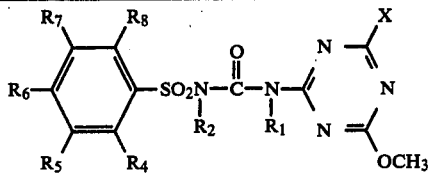

| R1 | R2 | R4 | R5 | R6 | R7 | R8 | X |
|---|---|---|---|---|---|---|---|
| CH(CH3)2 | CH3 | F | H | H | H | F | OCH(CH3)2 |
| CH(CH3)2 | CH3 | Cl | H | H | NO2 | H | C2H5 |
| OCH3 | CH3 | Br | H | H | H | H | OC2H5 |
| CH3 | n-C3H7 | Cl | H | H | Cl | H | OC2H5 |
| H | n-C3H7 | NO2 | H | H | H | H | OC2H5 |
| H | CH(CH3)2 | CF3 | H | H | H | H | OC2H5 |
| CH3 | CH(CH3)2 | Cl | H | H | H | H | OC2H5 |

TABLE IV-F

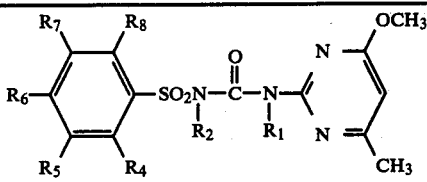

| R1 | R2 | R4 | R5 | R6 | R7 | R8 |
|---|---|---|---|---|---|---|
| H | CH3 | OCH3 | H | H | OCH3 | H |
| H | CH3 | Cl | H | H | H | H |
| H | CH3 | NO2 | H | H | H | H |
| H | CH3 | Cl | H | H | Cl | H |
| H | CH3 | CH3 | H | H | H | H |
| H | CH3 | Cl | H | F | H | H |
| H | CH3 | H | H | H | H | H |
| H | CH3 | CH3 | H | H | CH3 | H |
| H | CH3 | OC2H5 | H | H | OC2H5 | H |
| CH3 | CH3 | NO2 | H | H | CH3 | H |
| CH3 | CH3 | Cl | H | H | Cl | H |
| CH3 | CH3 | CH3 | H | H | Cl | H |
| CH3 | CH3 | CH3 | CH3 | H | CH3 | CH3 |
| CH3 | CH3 | OCH3 | H | H | H | H |
| CH3 | CH3 | F | H | H | F | H |
| C2H5 | CH3 | NO2 | H | H | H | H |
| C2H5 | CH3 | Cl | H | H | H | Cl |
| H | C2H5 | F | H | H | H | H |
| H | C2H5 | CF3 | H | H | H | H |
| H | C2H5 | OC2H5 | H | H | H | H |
| CH3 | C2H5 | OCH3 | H | H | OCH3 | H |
| CH3 | C2H5 | CH3 | H | H | NO2 | H |
| n-C3H7 | C2H5 | F | H | H | H | F |
| n-C3H7 | C2H5 | Br | H | H | H | H |
| CH(CH3)2 | C2H5 | CF3 | H | H | H | H |
| CH(CH3)2 | CH3 | Cl | H | H | OCH3 | H |
| n-C3H7 | CH3 | F | H | H | F | H |
| OCH3 | CH3 | CH3 | H | H | H | H |
| OCH3 | CH3 | Cl | H | H | H | H |
| CH3 | n-C3H7 | Cl | H | H | Cl | H |
| H | n-C3H7 | NO2 | H | H | H | H |
| H | CH(CH3)2 | CF3 | H | H | H | H |
| CH3 | CH(CH3)2 | Cl | H | H | H | Cl |

TABLE IV-G

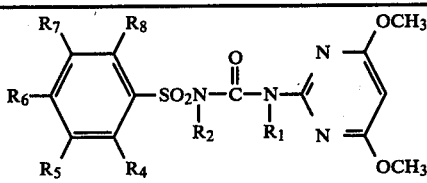

| R1 | R2 | R4 | R5 | R6 | R7 | R8 |
|---|---|---|---|---|---|---|
| H | CH3 | Cl | H | H | H | H |
| H | CH3 | NO2 | H | H | H | H |

TABLE IV-G-continued

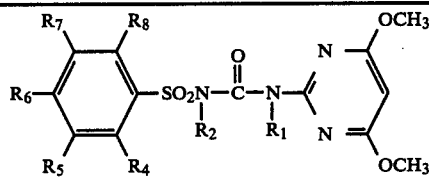

| R1 | R2 | R4 | R5 | R6 | R7 | R8 |
|---|---|---|---|---|---|---|
| H | CH3 | OCH3 | H | H | OCH3 | H |
| H | CH3 | CH3 | H | H | H | H |
| H | CH3 | H | H | H | H | H |
| CH3 | CH3 | NO2 | H | H | CH3 | H |
| CH3 | CH3 | Cl | H | H | Cl | H |
| H | CH3 | Cl | H | F | H | H |
| H | CH3 | OC2H5 | H | H | OC2H5 | H |
| H | CH3 | H | F | H | H | H |
| CH3 | CH3 | CH3 | H | H | Cl | H |
| CH3 | CH3 | CH3 | CH3 | H | CH3 | CH3 |
| CH3 | CH3 | OCH3 | H | H | H | H |
| CH3 | CH3 | F | H | H | F | H |
| C2H5 | CH3 | NO2 | H | H | H | H |
| C2H5 | CH3 | Cl | H | H | H | Cl |
| H | C2H5 | F | H | H | H | H |
| H | C2H5 | CF3 | H | H | H | H |
| H | C2H5 | OC2H5 | H | H | H | H |
| CH3 | C2H5 | OCH3 | H | H | OCH3 | H |
| CH3 | C2H5 | CH3 | H | H | NO2 | H |
| n-C3H7 | C2H5 | F | H | H | H | F |
| n-C3H7 | C2H5 | Br | H | H | H | H |
| CH(CH3)2 | C2H5 | CF3 | H | H | H | H |
| CH(CH3)2 | CH3 | Cl | H | H | OCH3 | H |
| n-C3H7 | CH3 | F | H | H | F | H |
| OCH3 | CH3 | CH3 | H | H | H | H |
| OCH3 | CH3 | Cl | H | H | H | H |
| CH3 | n-C3H7 | Cl | H | H | Cl | H |
| H | n-C3H7 | NO2 | H | H | H | H |
| H | CH(CH3)2 | CF3 | H | H | H | H |
| CH3 | CH(CH3)2 | Cl | H | H | H | Cl |

TABLE IV-H

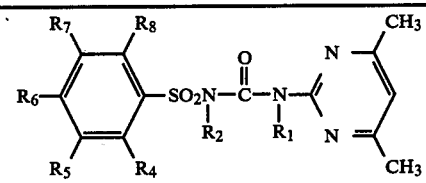

| R1 | R2 | R4 | R5 | R6 | R7 | R8 |
|---|---|---|---|---|---|---|
| H | CH3 | NO2 | H | H | H | H |
| H | CH3 | Cl | H | H | H | H |
| H | CH3 | CH3 | H | H | H | H |
| H | CH3 | OCH3 | H | H | OCH3 | H |
| H | CH3 | OC2H5 | H | H | OC2H5 | H |

TABLE IV-H-continued

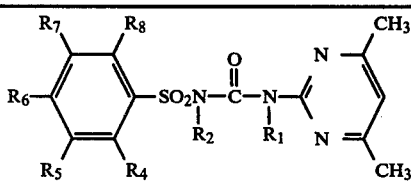

| R₁ | R₂ | R₄ | R₅ | R₆ | R₇ | R₈ |
|---|---|---|---|---|---|---|
| H | CH₃ | Cl | H | H | H | Cl |
| H | CH₃ | Cl | H | H | NO₂ | H |
| H | CH₃ | H | H | H | H | H |
| H | CH₃ | OCH₃ | H | H | H | H |
| CH₃ | CH₃ | Cl | H | H | Cl | H |
| CH₃ | CH₃ | NO₂ | H | H | CH₃ | H |
| CH₃ | CH₃ | CH₃ | H | H | Cl | H |
| CH₃ | CH₃ | CH₃ | CH₃ | H | CH₃ | CH₃ |
| CH₃ | CH₃ | OCH₃ | H | H | H | H |
| CH₃ | CH₃ | F | H | H | F | H |
| C₂H₅ | CH₃ | NO₂ | H | H | H | H |
| C₂H₅ | CH₃ | Cl | H | H | H | Cl |
| H | C₂H₅ | F | H | H | H | H |
| H | C₂H₅ | CF₃ | H | H | H | H |

TABLE IV-H-continued

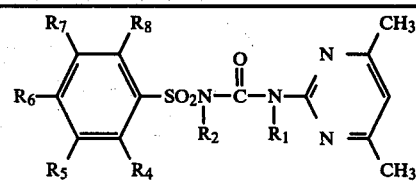

| R₁ | R₂ | R₄ | R₅ | R₆ | R₇ | R₈ |
|---|---|---|---|---|---|---|
| H | C₂H₅ | OC₂H₅ | H | H | H | H |
| CH₃ | C₂H₅ | CH₃ | H | H | NO₂ | H |
| CH₃ | C₂H₅ | OCH₃ | H | H | OCH₃ | H |
| n-C₃H₇ | C₂H₅ | F | H | H | H | F |
| n-C₃H₇ | C₂H₅ | Br | H | H | H | H |
| CH(CH₃)₂ | C₂H₅ | CF₃ | H | H | H | H |
| CH(CH₃)₂ | CH₃ | Cl | H | H | OCH₃ | H |
| n-C₃H₇ | CH₃ | F | H | H | F | H |
| OCH₃ | CH₃ | CH₃ | H | H | H | H |
| OCH₃ | CH₃ | Cl | H | H | H | H |
| CH₃ | n-C₃H₇ | Cl | H | H | Cl | H |
| H | n-C₃H₇ | NO₂ | H | H | H | H |
| H | CH(CH₃)₂ | CF₃ | H | H | H | H |
| CH₃ | CH(CH₃)₂ | Cl | H | H | H | Cl |

TABLE IV-I

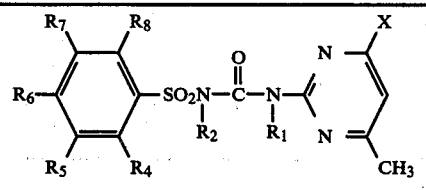

| R₁ | R₂ | R₄ | R₅ | R₆ | R₇ | R₈ | X |
|---|---|---|---|---|---|---|---|
| H | CH₃ | Cl | H | H | H | H | C₂H₅ |
| H | CH₃ | NO₂ | H | H | H | H | C₂H₅ |
| H | CH₃ | CH₃ | H | H | H | H | C₂H₅ |
| H | CH₃ | Cl | H | H | NO₂ | H | OC₂H₅ |
| H | CH₃ | NO₂ | H | H | CH₃ | H | OC₂H₅ |
| H | CH₃ | CH₃ | H | H | H | H | n-C₃H₇O |
| H | CH₃ | OCH₃ | H | H | H | H | SCH₃ |
| H | C₂H₅ | Cl | H | H | Cl | H | CH₂OCH₃ |
| CH₃ | CH₃ | F | H | H | H | H | C₂H₅ |
| CH₃ | CH₃ | CF₃ | H | H | H | H | C₂H₅ |
| CH₃ | CH₃ | CH₃ | H | H | CH₃ | H | OC₂H₅ |
| CH₃ | CH₃ | CH₃ | H | H | NO₂ | H | OC₂H₅ |
| CH₃ | CH₃ | H | H | H | H | H | CF₃ |
| C₂H₅ | CH₃ | F | H | H | F | H | OCH₂CH₂OCH₃ |
| C₂H₅ | CH₃ | Br | H | H | H | H | n-C₃H₇O |
| C₂H₅ | CH₃ | OCH₃ | H | H | OCH₃ | H | Cl |
| CH₃ | C₂H₅ | Cl | H | F | H | H | OC₂H₅ |
| C₂H₅ | C₂H₅ | NO₂ | H | H | CH₃ | H | CH₂OCH₃ |
| n-C₃H₇ | CH₃ | Cl | H | H | H | Cl | SCH₃ |
| n-C₃H₇ | CH₃ | OCH₃ | H | H | Cl | H | OC₂H₅ |
| OCH₃ | CH₃ | F | H | H | H | F | OCH(CH₃)₂ |
| CH(CH₃)₂ | CH₃ | Cl | H | H | NO₂ | H | C₂H₅ |
| CH₃ | n-C₃H₇ | Cl | H | H | Cl | H | OC₂H₅ |
| H | n-C₃H₇ | NO₂ | H | H | H | H | OC₂H₅ |
| H | CH(CH₃)₂ | CF₃ | H | H | H | H | OC₂H₅ |
| CH₃ | CH(CH₃)₂ | Cl | H | H | H | H | OC₂H₅ |

TABLE IV-J

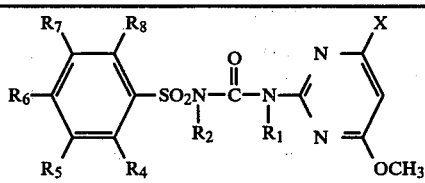

| R₁ | R₂ | R₄ | R₅ | R₆ | R₇ | R₈ | X |
|---|---|---|---|---|---|---|---|
| H | CH₃ | Cl | H | H | H | H | C₂H₅ |
| H | CH₃ | NO₂ | H | H | H | H | C₂H₅ |

TABLE IV-J-continued

[Structure: R7, R8 on benzene with R6, R5, R4; SO2N(R2)-C(O)-N(R1)-pyrimidine with X and OCH3]

| R1 | R2 | R4 | R5 | R6 | R7 | R8 | X |
|---|---|---|---|---|---|---|---|
| H | CH3 | CH3 | H | H | H | H | C2H5 |
| H | CH3 | Cl | H | H | NO2 | H | OC2H5 |
| H | CH3 | NO2 | H | H | CH3 | H | OC2H5 |
| H | CH3 | CH3 | H | H | H | H | n-C3H7O |
| H | CH3 | OCH3 | H | H | H | H | SCH3 |
| H | CH3 | Cl | H | H | Cl | H | CH2OCH3 |
| CH3 | CH3 | F | H | H | H | H | C2H5 |
| CH3 | CH3 | CF3 | H | H | H | H | C2H5 |
| CH3 | CH3 | CH3 | H | H | CH3 | H | OC2H5 |
| CH3 | CH3 | CH3 | H | H | NO2 | H | OC2H5 |
| CH3 | CH3 | H | H | H | H | H | CF3 |
| C2H5 | CH3 | F | H | H | H | H | OCH2CH2OCH3 |
| C2H5 | CH3 | Br | H | H | H | H | n-C3H7O |
| C2H5 | CH3 | OCH3 | H | H | OCH3 | H | Cl |
| CH3 | C2H5 | Cl | H | F | H | H | OC2H5 |
| C2H5 | C2H5 | NO2 | H | H | CH3 | H | CH2OCH3 |
| n-C3H7 | CH3 | Cl | H | H | H | Cl | SCH3 |
| n-C3H7 | CH3 | OCH3 | H | H | Cl | H | OC2H5 |
| CH(CH3)2 | CH3 | F | H | H | H | F | OCH(CH3)2 |
| CH(CH3)2 | CH3 | Cl | H | H | NO2 | H | OC2H5 |
| OCH3 | CH3 | Br | H | H | H | H | OC2H5 |
| CH3 | n-C3H7 | Cl | H | H | Cl | H | OC2H5 |
| H | n-C3H7 | NO2 | H | H | H | H | OC2H5 |
| H | CH(CH3)2 | CF3 | H | H | H | H | OC2H5 |
| CH3 | CH(CH3)2 | Cl | H | H | H | H | OC2H5 |

By using an appropriate N-(1,3,5-triazin-2-yl)-N-aminocarbonyl-2-thiophenesulfonamide or N-(pyrimidin-2-yl)-N-aminocarbonyl-2-thiophenesulfonamide, the compounds of Formula I set forth in Table V can be prepared by the procedure of Example 6. Alternatively, by using an appropriately substituted sulfonyl-N-alkyl-2-thiophenecarbamyl chloride and an appropriately substituted-2-aminopyrimidine or 2-amino-1,3,5-triazine, the same compounds of Formula I can be prepared by the procedure of Example 7.

TABLE V

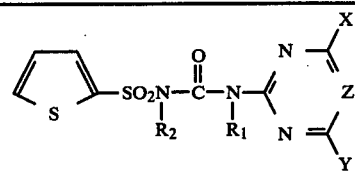

| R1 | R2 | X | Y | Z |
|---|---|---|---|---|
| H | CH3 | CH3 | CH3 | CH |
| H | CH3 | OCH3 | CH3 | CH |
| H | CH3 | OCH3 | OCH3 | CH |
| CH3 | CH3 | CH3 | CH3 | CH |
| CH3 | CH3 | OCH3 | CH3 | CH |
| CH3 | CH3 | OCH3 | OCH3 | CH |
| C2H5 | CH3 | CH3 | CH3 | CH |
| C2H5 | CH3 | OCH3 | CH3 | CH |
| n-C3H7 | CH3 | OCH3 | OCH3 | CH |
| —CH(CH3)2 | CH3 | OCH3 | CH3 | CH |
| OCH3 | CH3 | OCH3 | CH3 | CH |
| CH3 | C2H5 | OCH3 | CH3 | CH |
| CH3 | C2H5 | OCH3 | OCH3 | CH |
| C2H5 | C2H5 | OCH3 | CH3 | CH |
| H | CH3 | CH3 | CH3 | N |
| H | CH3 | OCH3 | CH3 | N |
| H | CH3 | OCH3 | OCH3 | N |
| CH3 | CH3 | CH3 | CH3 | N |
| CH3 | CH3 | OCH3 | OCH3 | N |
| CH3 | CH3 | OCH3 | CH3 | N |

TABLE V-continued

| R1 | R2 | X | Y | Z |
|---|---|---|---|---|
| C2H5 | CH3 | OCH3 | OCH3 | N |
| C2H5 | CH3 | OCH3 | CH3 | N |
| n-C3H7 | CH3 | OCH3 | OCH3 | N |
| CH(CH3)2 | CH3 | OCH3 | OCH3 | N |
| OCH3 | CH3 | OCH3 | CH3 | N |
| CH3 | C2H5 | CH3 | CH3 | N |
| C2H5 | C2H5 | OCH3 | OCH3 | N |
| H | C2H5 | OCH3 | CH3 | CH |
| H | C2H5 | OCH3 | OCH3 | N |
| H | CH3 | CH2OCH3 | OCH3 | CH |
| H | CH3 | CF3 | CH3 | CH |
| H | C2H5 | SCH3 | CH3 | CH |
| CH3 | C2H5 | OC2H5 | OCH3 | CH |
| H | CH3 | OC2H5 | OCH3 | N |
| H | CH3 | SCH3 | OCH3 | N |
| H | C2H5 | OCH2CH2OCH3 | OCH3 | N |
| CH3 | CH3 | n-C3H7O | CH3 | CH |
| C2H5 | CH3 | Cl | OCH3 | N |
| CH3 | n-C3H7 | OCH3 | CH3 | CH |
| H | n-C3H7 | OCH3 | OCH3 | N |
| H | CH(CH3)2 | OCH3 | CH3 | CH |
| CH3 | CH(CH3)2 | OCH3 | OCH3 | N |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of form a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

TABLE VI

| | PERCENT BY WEIGHT | | |
|---|---|---|---|
| | Active Ingredient | Diluent(s) | Surfactant(s) |
| Wettable powders | 20–90 | 0–74 | 1–10 |
| Oil Suspensions, Emulsions, Solutions (including Emulsifiable concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levers of active ingredient can, of course, by present depending on the intended use and the physical properties of the compound. Higher ratios of surfactant to active ingredient are sometimes desirable, and are achieved by incorporation into the formulation or by tank mixing.

Typical solid diluents are described in Watkins, et al, "Handbook of Insecticide Dust Diluents and Carriers", 2nd, Ed., Dorland Books, Caldwell, N.J. The more absorptive diluents are preferred for wettable powders and the denser ones for dusts. Typical liquid diluents and solvents are described in Marsden, "Solvents Guide", 2nd. Ed., Interscience, New York, 1950 Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, N.Y. 1963, pp 8–59ff.

For further information regarding the art of formulation, see for example:

H. M. Loux, U.S. Pat. No. 3,235,361, Feb. 15, 1966, Col. 6, Line 16 through Col. 7, Line 19 Examples 10–41.

R. W. Luckenbaugh, U.S. Pat. No. 3,309,192, Mar. 14, 1967, Col. 5, Line 43 through Col. 7 Line 62 and Examples 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Ed. Blackwell Scientific Publications, Oxford, 1968, pp. 101–103.

EXAMPLE 8

| Wettable Powder | |
|---|---|
| N—[N—(4,6-dimethoxy-1,3,5-triazin-2-yl)-N—methylaminocarbonyl]-2-chlorobenzenesulfonamide | 25% |
| Dioctyl sodium sulfosuccinate | 1.5% |
| Sodium ligninsulfonate | 3% |
| Low viscosity methyl cellulose | 1.5% |
| Attapulgite | 69% |

The ingredients are thoroughly blended, passed through an air mill, to produce an average particle size under 15 microns, reblended, and sifted through a U.S.S. No. 50 sieve (0.3 mm opening) before packaging.

EXAMPLE 9

| Wettable Powder | |
|---|---|
| N—[N—(4-methoxy-6-methylpyrimidin-2-yl)-N—methylaminocarbonyl]-2-chlorobenzenesulfonamide | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

EXAMPLE 10

| Wettable Powder | |
|---|---|
| N—[N—(4,6-dimethoxy-1,3,5-triazin-2-yl)-N—methylaminocarbonyl]-2-nitrobenzenesulfonamide | 80% |
| Sodium alkylnaphthalenesulfonate | 2% |
| Sodium ligninsulfonate | 2% |
| Synthetic amorphous silica | 3% |
| Kaolinite | 13% |

The ingredients are blended and hammer-milled to produce particles essentially all below 100 microns. The product is reblended, sifted through a U.S.S. No. 50 mesh screen and packaged.

EXAMPLE 11

| High Strength Concentrate | |
|---|---|
| N—[N—(4-methoxy-6-methylpyrimidin-2-yl)-N—methylaminocarbonyl]-2-nitrobenzenesulfonamide | 98.5% |
| Silica aerogel | 0.5% |
| Synthetic amorphous fine silica | 1.0% |

The ingredients are blended and ground in a hammer mill to produce a high strength concentrate essentially all passing a U.S.S. No. 50 sieve (0.3 mm opening). This material may then be formulated in a variety of ways.

EXAMPLE 12

| Aqueous Suspensions | |
|---|---|
| N—[N—(4-methoxy-6-methylpyrimidin-2-yl)-N—methylaminocarbonyl]-2-nitrobenzenesulfonamide | 40% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinyl alcohol | 1.0% |
| Water | 56.7% |

The ingredients are ground together in a sand mill to produce particles essentially all under five microns in size.

EXAMPLE 13

| Oil Suspension | |
|---|---|
| N—[N—(4,6-dimethoxy-1,3,5-triazin-2-yl)-N—methylaminocarbonyl]-2-nitrobenzenesulfonamide | 25% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 14

| Oil Suspension | |
|---|---|
| N—[N—(4-methoxy-6-methylpyrimidin-2-yl)-N—methylaminocarbonyl]-2-chlorobenzenesulfonamide | 35% |
| Blend of polyalcohol carboxylic esters and oil soluble petroleum sulfonates | 6% |
| Xylene | 59% |

The ingredients are combined and ground together in a sand mill to produce particles essentially all below 3 microns. The product can be used directly, extended with oils, or emulsified in water.

EXAMPLE 15

| Granule | |
|---|---|
| N—[N—(4,6-dimethoxy-1,3,5-triazin-2-yl)-N—methylaminocarbonyl]-2-chlorobenzenesulfonamide | 1% |
| Attapulgite granules (low volative matter, 0.71/0.31 mm U.S.S. # 25–50 sieves) | 99% |

The active ingredient is warmed to approximately 80° C. and sprayed upon dedusted and pre-warmed attapulgite granules in a double-cone blender. The granules are then allowed to cool and are packaged.

EXAMPLE 16

| Granule | |
|---|---|
| Wettable powder of Example 9 | 5% |
| Attapulgite granules (U.S.S. # 20–40; 0.84–0.42 mm) | 95% |

A slurry of wettable powder containing 50% solids is sprayed on the surface of attapulgite granules in a double-cone blender. The granules are dried and packaged.

EXAMPLE 17

| Extruded Pellet | |
|---|---|
| N—[N—(4,6-dimethoxy-1,3,5-triazin-2-yl)-N—methylaminocarbonyl]-2-nitrobenzenesulfonamide | 25% |
| Anhydrous soidum sulfate | 10% |
| Crude calcium ligninsulfonate | 5% |
| Sodium alkylnaphthalenesulfonate | 1% |
| Calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm opendings). The granules held on a U.S.S. No. 40 sieve (0.42 mm openings) may be packaged for use and the fines recycled.

UTILITY

The compounds of Formula I are useful for the selective control of undesired vegetation in crops such as rice, wheat, and barley. These compounds are most effective when applied after emergence of weeds from the soil. However, they are also effective when applied preemergence. In addition, they can be used as directed treatments for the pre/post-emergence control of weeds in various crops. These compounds are also useful wherever general weed control is required, such as industrial sites, railroad and utility rights-of-way, along fences, building foundations, parking and storage lots, etc.

The precise amount of the compounds of Formula I to be used in any given situation will vary according to the particular end result desired, the use involved, the crop weed species, and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.03 to about 15 kilograms, preferably about 0.12 to about 8, per hectare. The lower rates in this range will generally be selected on lighter soils, soils low in organic matter content, for selective weed control in crops, or in situations where maximum persistance is not necessary.

Although the compounds of the present invention provide excellent weed control when applied in the sole herbicide treatment, they may be advantageously applied in combination with other herbicides, including, but not restricted to, the following:
Methyl-2-//4-/2,4-dichlorophenoxy/phenoxy//-propanoate;
Carbamic acid diisopropylthiol-S-/2,3,3-trichloroalkyl/ester;
1,2-dimethyl-3,5-diphenyl-pyrazolium methyl-sulfate;

Ethyl-N-benzoyl-N-/3,4-dichlorophenyl-2-aminopropanoate;
Diisopropylthiolcarbamic acid, ester with 2,3-dichloroallyl alcohol;
4-Chloro-2-butynyl-m-chlorocarbanilate;
2,4-dichlorophenoxyacetic acid (and derivatives);
3-chloro-2-(4-chloro-2-fluorophenyl)-4,5,6,7-tetrahydro-2H-indazole;
3-isopropyl-1(H)-benzo-2,1,3-thiadizin-4-one-2,2-dioxide;
S-(4-chlorobenzyl)-N,N-diethylthiolcarbamate;
2-chloro-2',6'-diethyl-N-butoxymethyl-acetanilide;
3',4'-dichloropropionanilide;
2,4,6-trichlorophenyl-4'-nitrophenyl ether;
5-tert-butyl-3-(2,4-dichloro-5-isopropoxyphenyl)-1,3,4-oxadiazol-2-one The herbicidal activity of compounds of this invention was discovered in greenhouse tests, conducted as explained below.

Test 1

Seeds of crabgrass (*Digitaria* spp.), barnyardgrass (*Echinochloa crusgalli*), wild oats (*Avena fatua*), *Cassia Tora*, morningglory (*Ipomoea* spp.), cocklebur (*Xanthium* spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

The ratings for compounds tested by this procedure are recorded in Table VII, and consists of a number and a letter. The number describes the extent of the response and ranges from zero to ten, with zero representing no response and ten representing 100% response. The letter describes the type of response, with "B" representing burn (acute response), "C" chlorosis-necrosis (chronic response), "E" emergence inhibited, "G" growth retarded, "H" formative effect (malformation or hormone type), "L" lodging, and "U" unusual pigmentation (other than dark green color). However, the combined rating "6Y" is an exception to the extent and type explanation given above, in that it simply represents abscised buds or flowers.

| | | | POST EMERGENCE | | | | | | | | | | | | |
|---|---|---|---|---|---|---|---|---|---|---|---|---|---|---|---|
| | Rate, kg/ha | BUSH BEAN | COTTON | SOR- GHUM | CORN | SOY- BEAN | WHEAT | WILD OATS | RICE | BARN- YARD GRASS | CRAB- GRASS | MORN- ING- GLORY | COCLEBUR | CASSIA | NUT- SEDGE |
| R = Cl | 2 | 4H | 2U 2C 9G | 0 | 7H | 6C 9G | 0 | 0 | 0 | 1C 9H | 4G | 5C 9G | 9C | 5C 9G | 4C 9G |
| $NO_2$ | 2 | 3C 8G 6Y | 9C | 4G | 3C 9G | 3C 9G | 1C | 2C | 1C 6G | 5C 9G | 4C 8G | 9C | 9C | 9C | 5C 8G |
| | .4 | 4H 6G 6Y | 9C | 2G | 3H 9G | 4C 9G | 0 | 0 | 3G | 2C 7G | 9C | 9C | 9C | 8C | 5C 8G |
| | 2 | 1C | 1C 1H | 0 | 0 | 0 | 0 | 0 | 0 | 0 | 0 | 0 | 0 | 0 | 0 |
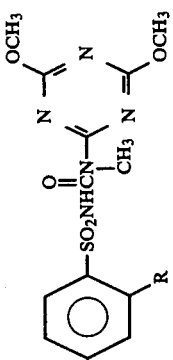
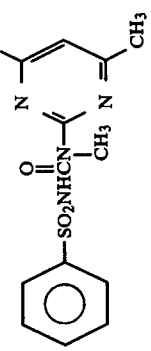

PRE-EMERGENCE
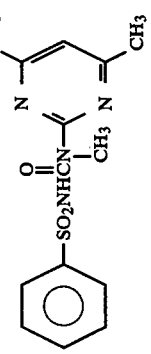
| R= | Rate, kg/ha | SORGHUM | CORN | SOYBEAN | WHEAT | WILD OATS | RICE | BARN-YARD GRASS | CRAB-GRASS | MORNING-GLORY | COCKLEBUR | CASSIA | NUT-SEDGE |
|---|---|---|---|---|---|---|---|---|---|---|---|---|---|
| Cl | 2 | 0 | 3G | 9H | 0 | 0 | 1C 3G | 3C 9H | 4G | &E | 9H | &E | 5G |
| NO$_2$ | 2 | 5G | 2C 7G | 9H | 0 | 2C | &E | 2C 9G | 9G | 9G | 9E | 9G | &E |
|  | .4 | 0 | 1C 9G | 9H | 0 | 2G | 9H | 2C 9G | 1C 5G | 9G | 9G | 9G | &E |
|  | 2 | 0 | 2C | 1C | 0 |  | 2G | 2G | 0 | 1C | 0 | 2C | 0 |

Test 2

The data from Test 2 are presented in Table VIII to illustrate further the biological activity of the compounds of this invention. They illustrate the herbicidal efficacy of the compounds with selectivity for an important crop rice.

The test compounds were applied in a non-phytotoxic solvent to soil pots containing seeds of an intermediate hybrid rice, japonica rice, barnyardgrass (*Echinochloa crusgalli*), and morningglory (*Ipomoea sp.*). Established plantings (postemergence) of the species mentioned above were also included in the test. The plants were maintained in a greenhouse (glasshouse), and visual plant response ratings (as described for Table VII) were taken four weeks after application.

X is Cl, $CH_3$, $-CH_2CH_3$, alkoxy of one to three carbons, $CF_3$, $CH_3S-$, $CH_3OCH_2-$ or $CH_3OCH_2CH_2O-$;

Y is $CH_3$ or $OCH_3$;

Z is CH or N;

and their agriculturally suitable salts; provided that:

a. $R_1$ and $R_2$ may not simultaneously be hydrogen; and b. when $R_4$ and $R_8$ are both hydrogen, at least one of $R_5$, $R_6$ or $R_7$ must be hydrogen;

c. when $R_6$ is H and all or $R_4$, $R_5$, $R_7$ and $R_8$ are other than H, then all of $R_4$, $R_5$, $R_7$ and $R_8$ must be either Cl or $CH_3$; and d. when $R_6$ is other than H, at least one of $R_4$, $R_5$, $R_7$ and $R_8$ is other than H and at least two of $R_4$, $R_5$, $R_7$ and $R_8$ must be hydrogen.

TABLE VIII

| COMPOUND | kg ai/ha | Preemergence ||||  Postemergence ||||
|---|---|---|---|---|---|---|---|---|---|
|  |  | Intermediate Rice | Japonica Rice | Barnyardgrass | Morningglory | Intermediate Rice | Japonica Rice | Barnyardgrass | Morningglory |
| 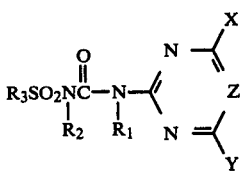 | ¼ | 0 | 0 | 0 | 0 | 0 | 0 | 0 | 10B |
|  | ½ | 0 | 0 | 0 | 0 | 0 | 0 | 0 | 10B |
|  | 1 | 0 | 0 | 0 | 0 | 0 | 0 | 0 | 10B |
|  | 2 | 0 | 0 | 0 | 0 | 0 | 0 | 4G | 10B |
| 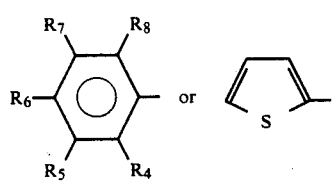 | ⅛ | 0 | 0 | 0 | 0 | 0 | 0 | 0 | 10B |
|  | ¼ | 0 | 0 | 0 | 0 | 0 | 0 | 0 | 10B |
|  | ½ | 0 | 0 | 0 | 0 | 0 | 0 | 0 | 10B |
|  | 1 | 0 | 0 | 0 | 0 | 0 | 0 | 6B5L | 10B |

What is claimed is:

1. A compound having the formula:

$$R_3SO_2NC-N \begin{array}{c} X \\ N \\ Z \\ Y \end{array} \quad (I)$$

wherein $R_1$ is H, alkyl of one to three carbon atoms or $-OCH_3$;

$R_2$ is H or alkyl of one to three carbon atoms;

$R_3$ is

[phenyl ring with $R_4$, $R_5$, $R_6$, $R_7$, $R_8$ substituents] or [thiophene ring with S]

$R_4$ and $R_7$ are independently hydrogen, fluorine, chlorine, bromine, alkyl of 1-4 carbon atoms, alkoxy of 1-4 carbon atoms, nitro, $CF_3$, $CH_3S-$ or $CH_3CH_2S-$;

$R_5$, $R_6$ and $R_8$ are independently hydrogen, fluorine, chlorine, bromine or methyl;

2. A compound of claim 1 wherein
$R_1$ and $R_2$ are independently H or $CH_3$;
X is $CH_3$, $CH_3CH_2-$ or alkoxy of one to three carbons; and
Y is $CH_3$ or $OCH_3$.

3. A compound of claim 2 wherein
$R_1$ is $CH_3$;
$R_2$ is H; and
X and Y are independently $CH_3$ or $OCH_3$.

4. A compound of claim 3 wherein
X is $OCH_3$; and
Y is $CH_3$ or $OCH_3$.

5. A composition suitable for controlling the growth of undesired vegetation which comprises an effective amount of a compound of chain 1 and at least one of the following: surfactant, solid or liquid diluent.

6. A composition suitable for controlling the growth of undesired vegetation which comprises an effective amount of a compound of claim 1 and at least one of the following: surfactant, solid or liquid diluent.

7. A composition suitable for controlling the growth of undesired vegetation which comprises an effective amount of a compound of claim 3 and at least one of the following: surfactant, solid or liquid diluent.

8. A composition suitable for controlling the growth of undesired vegetation which comprises an effective amount of a compound of claim 4 and at least one of the following: surfactant, solid or liquid diluent.

9. A method for controlling the growth of undesired vegetation which comprises applying to the locus to be protected an effective amount of a compound of claim 1.

10. A method for controlling the growth of undesired vegetation which comprises applying to the locus to be protected an effective amount of a compound of claim 2.

11. A method for controlling the growth of undesired vegetation which comprises applying to the locus to be protected an effective amount of a compound of claim 3.

12. A method for controlling the growth of undesired vegetation which comprises applying to the locus to be protected an effective amount of a compound of claim 4.

* * * * *